United States Patent [19]

Vassilev et al.

[11] 4,063,892

[45] Dec. 20, 1977

[54] METHOD FOR THE EARLY DIAGNOSIS OF CANCER

[75] Inventors: Vassil Ivanov Vassilev; Hristo Vladimirov Goranov; Sivcho Hristov Sivchev, all of Sofia, Bulgaria

[73] Assignee: Nauchno-Proizvodstveno Obedinenie po Veterinarno Delo, Sofia, Bulgaria

[21] Appl. No.: 682,963

[22] Filed: May 3, 1976

[30] Foreign Application Priority Data

May 5, 1975 Bulgaria .................................. 29867

[51] Int. Cl.$^2$ ...................... G01N 33/16; G01N 21/02
[52] U.S. Cl. .................................... 23/230 B; 356/51; 424/7
[58] Field of Search ........................ 23/230 B; 356/51; 424/7

[56] References Cited

U.S. PATENT DOCUMENTS

| | | | |
|---|---|---|---|
| 3,327,119 | 6/1967 | Kamentsky | 356/51 X |
| 3,988,115 | 10/1976 | Modabber | 23/230 B |
| 3,999,944 | 12/1976 | Grosser | 23/230 B |

Primary Examiner—Sidney Marantz
Attorney, Agent, or Firm—Karl F. Ross

[57] ABSTRACT

A method of detecting cancer in humans in which a blood sample is processed to recover the plasma from cellular matter and is then treated with aluminum oxide adsorbent and diluted. The diluted sample is subjected to spectrophotometric analysis at wavelengths of 562, 576 and 610 nm before and after dilution. The decrease in the extinction value A of the measurement at 576 mn, the difference B between the extinction values at 562 and 610 nm of the diluted sample and the value C constituting the difference between the changes in extinction values at 576 to 562 nm in the two measurements is determined and a coefficient is obtained where $K = (A \times B/C)$. A value K of less than 95 is indicative of a statistically significant possibility of cancer while a value above 105 has a statistically significant probability of lack of neoplasm.

3 Claims, No Drawings

METHOD FOR THE EARLY DIAGNOSIS OF CANCER

The invention concerns a method for the early diagnosis of cancer in humans.

It is known that cancer cells have macromolecular structures that are more or less specific and in some cases common to the various types of neoplasms. This has been concretely demonstrated by cross immune reactions. In most cases these macromolecules are released from the interior of the cancer cell or from its surface and can be detected in the blood plasma where their concentration or activity depends to a certain extent on the development of the cancer tissue, and its locale.

As most of the macromolecules possess antigenic properties their presence in the blood plasma has permitted a number of methods for the immunodiagnosis of neoplastic diseases in human beings.

Such methods are:

Investigation of the serum alphafetoprotein, which is present in a higher level in people with cancer. This method can be used only for the differing diagnosis only of testis and liver tumors.

Isolation of the cancer-embryonal antigen as developed Gold and Friedman. Based on this antigen's conjugation with radioactive iodine and the determination of the specific radioactivity, the method gives good results in diagnosing cancer of the large intestines and the rectum as well as that of the pancreas. With tumors located elsehwere, however, the effectiveness of the method considerably lower. The average detection capacity of the method is 62 percent. It is disadvantageous in that it has a rather low detection ability in the early stages of the cancer development, and, therefore, cannot be employed in a screening test. Besides, it yields positive results in 30 percent of cases having an inflammatory processes of the lungs and cases involving gastrointestinal tract as well as in 25 percent of the habitual smokers.

Determination of the beta-S-fetoprotein, which is present in increased amounts in the serum of patients with hepatocarcinoma, cancer of the stomach, and leukemia. However, as is the case with to the other fetal antigens, higher levels of this antigen are also found in nonmalignant diseases of the liver (e.g. cirrhosis).

The method described by Boerklund., making use of the changes in the amount of the polypeptides that are specific to malignant tumors. It gives a good percent of detection in cases of malignant tumors with metastases, i.e. about 79%, but is to a large extent ineffective in the case of primary untreated neoplasms without metastases, i.e. about 43%. In addition, in about 21 percent of the noncancer patients this method positive for malignant diseases. The total detection percent with the various malignant neoplasms is 66%.

An analysis of the detection capacity of the immunodiagnostic tests known so far and described above has shown that they all are based on the presence of substances (agents) having antigenic properties, specific to individual organs or types of neoplasms. Because of this they cannot detect various types of malignant neoplasia in the remaining organs and tissues or have only a low percent of detection. It is not uncommon that a high percent of cancer-positive results are obtained in the case of non-cancer diseases of the respective organs. Because these methods are all associated with the level of a particular antigen substance in the blood plasma, the positive response of the respective test usually corresponds to the later developmental stages of the cancer process.

The object of the present invention is to provide a simple and effective method for the detection of cancer-affected persons in the early stages of the disease process, with neoplasms of different types and with neoplastic formations, at different locations.

It has now been found that in about 40–50 percent of people with cancer there are characteristic changes in the physicochemical behavior of some unidentified molecules of the blood plasma, manifested at definite wavelengths of the visible region of the spectrum.

The a method of the invention is principally based on the state changes of molecules or molecular complexes in the blood plasma after the use of an ion exchange adsorbent and dilution at which the ratio between the extinction values, is measured at wavelengths of 562, 576 and 610.

Acid aluminum oxide, prepared as described by Brockmann, serves as an ion exchange adsorbent, and is used by manual mixing with the plasma or as a standard adsorption column with an inner diameter of 6 mm, the adsorption layer being 2 cm high, and the entire column — 10 cm in length. Distilled water is used as an extender or still better is natural mineral water (socalled Mihalkovska voda).

In accordance with the invention the method consists in the following:

Blood plasma is obtained from venous blood stabilized with EDTA at the rate of 2 mg per ml following centrifugation at 5000 r.p.m. in the course of 5 minutes. The plasma is removed through gentle sucking by means of a syringe, care being taken not to take up the coat of leukocytes formed over the erythrocyte sediment, and is then again centrifuged under the same conditions. Blood is invariably taken from a patient on an empty stomach. No samples should be used that show signs of lipemia or hemolysis. The samples are thus free from cells or cell fragments. The plasma thus obtained is treated in one of the following ways:

a. As much as two mililiters of the plasma under study is placed in a round bottom centrifuge test tubes, adding to it standard acid aluminum oxide (Brockmann) in an amount of 200 mg per ml plasma. The tube is shaken intensively at room temperature for three minutes, followed by centrifugation at 5000 r.p.m. for 5 min. The supernatant plasma is withdrawn by suction and transferred to another clean tube and is again centrifuged under the same conditions to eliminate residual aluminum oxide. A little more than 1 ml plasma is taken and its extinctions are measured at wavelengths of 562, 576 and 610 nm in a cuvette of 1 cm thickness of the layer against the air. The data obtained are referred to as stage "0".

b. Two milimeters of plasma is allowed to pass freely through a standard adsorption microcolumn charged with acid aluminum oxide (Brockmann). The extinctions are then measured as in (a).

Next as much as 1 is placed in a centrifuge tube and the extinctions are measured after adding to the plasma 0.5 ml of a; standard diluent (distilled water or Mihalkovska voda). The system is mixed thoroughly for 3 min at room temperature, and is centrifuged at 5000 r.p.m. for 5 min. The content of the tube is poured into a cuvette (care being taken not ot absorb the occasionally forming sediment) and the extinction values are recorded at the wavelengths measured above, and the results obtained are referred to as data at stage "P".

The differentiation between cancer-free and cancer-affected patients is performed on the basis of the data obtained, and more specifically, by means of a coefficient calculated in a way in which the extinction values are made use of as whole numbers (e.g. 348 stands for 0.348). Calculated are:

A = decrease of the extinction value in stage "P" (wavelength 576 nm) expressed in percent of the extinction value in stage "O" (same wavelength) referred to as 100 percent;

B = difference between the extinction values measured at wavelengths of 562 nm and 610 nm in stage "P";

C = difference between delta 576-562 nm in stage "O" and delta 576-562 in stage "P".

The data obtained are further processed to calculate a coefficient: whereby the A value is multiplied by the B value, and the resulting value is divided by the C value. The limiting value of the coefficient thus arrived at between cancer-affected and normal people is 100. Statistically significant for diseased persons are values that are below 95; for healthy persons statistically significant are the values above 105. Coefficients in the 95 - 105 range have low order of significance and are defined as limiting; they are to be studied for a second time.

A model performance of the method, and the record kept of the results obtained is as follows:

a. Plasma of a normal person;

| wavelengths nm | stages "O" | "P" |
|---|---|---|
| 562 | 0.243 | 0.184 |
| 576 | 0.282 | 0.211 |
| 610 | 0.150 | 0.117 |

Therefore:

$$A = 100 - \left(\frac{211 \times 100}{282}\right) = 100 - 74.82 = 25.18 \text{ percent};$$

$$B = 184 - 117 = 67;$$

$$C = (282 - 243) - (211 - 184) = 39 - 27 = 12;$$

$$K = \frac{25.18 \times 67}{12} = 140.59$$

b. Plasma of a cancer-affected person

| wavelengths nm | stages "O" | "P" |
|---|---|---|
| 562 | 0.196 | 0.157 |
| 576 | 0.244 | 0.188 |
| 610 | 0.126 | 0.108 |

Therefore:

$$A = 100 - \left(\frac{188 \times 100}{244}\right) = 100 - 77.05 = 22.95 \text{ percent};$$

$$B = 157 - 108 = 49;$$

$$C = (244 - 196) - (188 - 157) = 48 - 31 = 17;$$

$$K = \frac{22.95 \times 49}{17} = 66.15$$

The method was applied to investigate 74 clinically normal persons 70 of which showed coefficient values above 105; this corresponds to 94.6 percent detection.

One hundred thirty-nine out of the 168 patients examined in the initial phases of neoplastic diseases (manifesting no metastases) showed coefficient values below 95; this corresponds to 82.7 percent detection. Table 1 presents data obtained from cancer-affected patients that were examined and grouped in accordance with the locale of the neoplasm.

In addition to cancer-affected and clinically normal persons this method was applied also to people suffering from other diseases.

Forty-eight out of 58 such people with inflammatory and noninflammatory diseases showed coefficient (K) values above 105; ten persons; showed values below 95. The percent of detection in this case corresponds to 17.24.

The diluent has the following preferred composition:

|  | mg/l | meq V % |
|---|---|---|
| ANIONS | | |
| Fluorine | 3.2 | 0.41 |
| Chlorine | 66.8 | 4.60 |
| Sulphate | 313.4 | 15.92 |
| Bicarbonate | 1977.1 | 79.07 |
|  | mg/l | meq V % |
| CATIONS | | |
| Sodium | 576.8 | 61.20 |
| Potassium | 30.0 | 1.87 |
| Calcium | 297.1 | 27.89 |
| Magnesium | 45.0 | 9.04 |
| Ac metasalicylicum | 91.0 | |
| Ac metaboricum | 5.2 | |
| pH = 6.10. | | |

We claim:

1. A method of detecting cancer in humans which comprises the steps of:

a. obtaining a blood sample from a patient to be screened for cancer;

b. separating cellular matter from the blood plasma of said sample;

c. treating said blood plasma with Brockmann aluminum oxide;

d. subjecting a portion of the plasma treated with Brockmann aluminum oxide to spectrophotometric analysis at wavelengths of 562, 576 and 610 nm to obtain first extinction values at each of said wavelengths;

e. diluting another portion of the plasma treated with Brockmann aluminum oxide to dilution with a standard diluent to produce a diluted specimen;

f. subjecting said diluted specimen to spectrophotometric analysis at wavelengths of 562, 576 and 610 nm to obtain respective second values of total extinction at said wavelengths;

g. deriving a value A corresponding to the percentage decrease in the first and second values at said wavelengths of 576 nm deriving a value B corresponding to the difference in the extinction of second values between the wavelengths of 562nm and 610 nm, and deriving a value C corresponding to the difference between the change in first extinction values at 576 nm to 562 nm and the change in said second values from 576 nm to 562 nm; and h. deriving a coefficient $K = (A + B/C)$ where a K value less than 95 represents a statistically significant probability of cancer and a K value above 105 represents a statistically significant probability absence of cancer.

2. The method defined in claim 1 wherein said diluent is distilled water.

3. The method defined in claim 1 wherein the diluent used represents a natural liquid product having approximately the following composition:

|  | mg/l | meq V % |
|---|---|---|
| ANIONS | | |
| Fluorine | 3.2 | 0.41 |
| Chlorine | 66.8 | 4.60 |
| Sulphate | 313.4 | 15.92 |
| Bicarbonate | 1977.1 | 79.07 |
| CATIONS | | |
| Sodium | 576.8 | 61.20 |
| Potassium | 30.0 | 1.87 |
| Calcium | 297.1 | 27.89 |
| Magnesium | 45.0 | 9.04 |
| Ac metasalicylicum | 91.0 | |
| Ac metaboricum | 5.2 | |
| pH = 6.10. | | |

* * * * *